US006795524B2

(12) United States Patent
Hayashi

(10) Patent No.: US 6,795,524 B2
(45) Date of Patent: Sep. 21, 2004

(54) X-RAY DIAGNOSIS APPARATUS AND CONTROL METHOD THEREOF

(75) Inventor: Takashi Hayashi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/962,161

(22) Filed: Sep. 26, 2001

(65) Prior Publication Data

US 2002/0041654 A1 Apr. 11, 2002

(30) Foreign Application Priority Data

Sep. 26, 2000 (JP) ........................................ 2000-292371

(51) Int. Cl.[7] ............................................ G01R 33/563
(52) U.S. Cl. ................................ 378/98.12; 378/98.11; 378/98.2
(58) Field of Search .............................. 378/196, 98.12, 378/98.11, 98.2, 62; 382/130, 128

(56) References Cited

U.S. PATENT DOCUMENTS

| | | | | |
|---|---|---|---|---|
| 4,613,983 A | * | 9/1986 | Yedid et al. | 378/98.12 |
| 5,631,942 A | * | 5/1997 | Shinoda | 378/98.12 |
| 5,833,607 A | * | 11/1998 | Chou et al. | 600/407 |
| 6,052,476 A | * | 4/2000 | Qian et al. | 382/130 |
| 6,195,450 B1 | * | 2/2001 | Qian et al. | 382/130 |
| 6,426,994 B1 | * | 7/2002 | Van Vaals | 378/98.12 |

OTHER PUBLICATIONS

T. Taruoka, et al., "Long–Range DSA Based on Bloodstream Chasing", Image Information, May 1990 (Japan), pp. 591–597.

Hisato Sato, et al., "Peripheral Stepping DSA on Multi–purpose X–ray Equipment: POLYSTAR", Abstracts of Reported Treatises of JMCP, 1995 (Japan), p. 1121.

Shinji Okano, et al., "Clinical Evaluation of DIGITEX2400 Stepping DSA for Peripheral Angiography", Abstracts of Reported Treatises, Sep. 1996 (Japan), p. 1097.

* cited by examiner

Primary Examiner—David V. Bruce
Assistant Examiner—Hoon Song
(74) Attorney, Agent, or Firm—Oblon, Spivak, McClelland, Maier & Neustadt, P.C.

(57) ABSTRACT

An angiography apparatus includes a bed having a top on which a patient to be examined lies down, a substantially C-shaped C-arm, and an X-ray generating means and X-ray detection means which are arranged to oppose one end and the other end of the C-arm. According to this angiography apparatus, in chasing and imaging the flow of a contrast medium injected into the patient, the C-arm 3 can be arbitrarily moved in a direction. In addition, according to the angiography apparatus of this invention, by displaying a simulated image of the flow of the contrast medium, an operator can simulate contrast medium chase imaging before actual contrast medium chase imaging.

13 Claims, 12 Drawing Sheets

X-RAY DIAGNOSIS APPARATUS AND CONTROL METHOD THEREOF

CROSS-REFERENCE TO RELATED APPLICATIONS

This application is based upon and claims the benefit of priority from the prior Japanese Patent Application No. 2000-292371, filed Sep. 26, 2000, the entire contents of which are incorporated herein by reference.

BACKGROUND OF THE INVENTION

1. Field of the Invention

The present invention relates to an X-ray image diagnosis apparatus and control method thereof which can execute contrast medium chase imaging without imposing an excessive burden of application of X-rays and injection of a contrast medium on a patient to be examined.

2. Description of the Related Art

A conventional X-ray image diagnosis apparatus for imaging a blood vessel with contrast enhanced by a contrast medium is known, which includes, for example, a substantially C-shaped support unit (to be referred to as a "C-arm" hereinafter) and an X-ray tube serving as an X-ray source and an image intensifier (I.I.) serving as a detector which are arranged on one end and the other end of the C-arm, an image processing unit for processing acquired projection data, and the like.

Conventionally, as this X-ray image diagnosis apparatus, an apparatus having a contrast medium chase imaging function (so-called bolus-chase imaging function) is known. This contrast medium chase imaging is an imaging technique of checking, for example, the manner in which a contrast medium injected into a patient from a predetermined region flows in the patient. In the case of lower extremity imaging, for example, to check the manner in which a contrast medium injected into a patient from an abdomen as the predetermined region flows in the patient up to the ends (i.e., the tiptoes) of the two legs, this function serves to realize movement of the C-arm between these two regions and execute X-ray imaging along this movement.

In order to execute the above contrast medium chase imaging, an imaging start position and end position are checked in advance. In the above case, the imaging start position coincides with the "abdomen", and the imaging end position coincides with "ends of the two legs" (if, however, the imaging means is, for example, a so-called "bolus chase DSA mode", the imaging start position of a mask image may be the "ends of the two legs", and settings for them can be flexibly made). In addition, this imaging start position is checked on the basis of fluoroscopically sensed images.

An operator performs actual contrast medium chase imaging while manually changing the position of the C-arm at a position between the imaging start position and the imaging end position through an appropriate input means such as a jog-shuttle.

According to the above contrast medium chase imaging function described above, only imaging upon "movement in one direction" from the contrast medium injection position to the direction in which the contrast medium flows can be performed. More specifically, according to the prior art, when, for example, the two legs are to be imaged, imaging of the two legs is generally executed in one direction. Assume that the contrast medium flows at different flow rates in the two legs. In this case, even if an accurate contrast medium chase can be made in one leg, the purpose of operation cannot be sometimes attained in the other leg.

For example, a reason for this is that in executing subtraction processing between an X-ray image (mask image) including no contrast medium (image) and an X-ray image (contrast or live image) including a contrast medium (image), it is difficult to simultaneously perform this subtraction processing and flexible movement of the C-arm, i.e., real-time subtraction processing.

A case where a contrast medium flows at different flow rates in the respective legs includes a case where a blood vessel (a portion) in one leg is shorter than that in the other leg, a case where a morbid portion exists in the blood vessel, and a case where some kind of anomaly is present on the inner wall of the blood vessel. In addition, the flow of a contrast medium may completely stagnate depending on the state of a morbid portion or the like (occlusion of the blood vessel).

In the prior art, therefore, in the above case, after the C-arm is moved up to the tiptoe position, or the presence of a morbid portion is recognized, a series of imaging operations must be performed from the beginning to image the other leg. According to this operation, however, the patient is exposed to X-rays twice, and a contrast medium must be injected into the patient twice, resulting an excessive burden on the patient.

In addition, the manner in which a contrast medium flows and its flow rate varies among patients to be examined regardless of whether the above morbid portion and the like exist. For these reasons, contrast medium chase imaging is basically performed manually, as described above. In general, the manner in which a contrast medium flows greatly varies among patients, and hence an operator needs to have a certain degree of skill in performing the above manual operation in order to make a successful chase.

According to the prior art, therefore, there are many cases where contrast medium chase imaging cannot be successfully done in one cycle. As a consequence, re-imaging must be done.

To perform the above re-imaging is to expose a patient to X-rays twice and inject a contrast medium into the patient twice. Such operation is not preferable.

The present invention has been made in consideration of the above situation, and has as its patient to provide an X-ray image diagnosis apparatus which can execute contrast medium chase imaging without imposing an excessive burden of exposing a patient to the examined to X-rays and injecting a contrast medium into the patient.

The present invention has the following means to solve the problems described below.

According to the first aspect of the invention, there is provided an X-ray diagnosis apparatus comprises: a bed on which a patient lies down; a support unit including an X-ray generator configured to emit X-ray to the patient and an X-ray detector configured to detect the X-ray emitted form said X-ray generator; a movement mechanism configured to change a relative position of said support unit to said the patient; a position detector configured to detect the relative position; and a memory configured to acquire an information with respect to the relative position from said position detector at timing of the X-ray emitting and store the information connected to a first X-ray image when the first X-ray image is acquired by emitting X-ray to the patient with changing the relative position in a first direction.

According to the second aspect of the invention, there is provided an X-ray diagnosis apparatus comprises: a memory configured to store a plurality of images each of which is added an information with respect to a relative position of a support unit to a patient and includes a simulated flow of a contrast medium; a image generator configured to generate a moving image, in which a contrast medium looks as if it actually flowed, by pasted the plurality of images together on the basis of the information; a display device configured to display the moving image; and an input device configured to move a field of view on the moving image in accordance with the flow of the contrast medium.

According to the third aspect of the invention, there is provided a control method of X-ray diagnosis apparatus comprises: acquiring a first image by emitting X-ray to a patient with changing a relative position of a support unit to the patient in a first direction, the support unit including an X-ray generator and an X-ray detector configured to detect X-ray emitted form said X-ray generator; acquiring an information with respect to the relative position of said support unit to said the patient at the timing of the X-ray emitting; storing the information connected to the first image; and controlling movement of said support unit on the basis of the stored information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
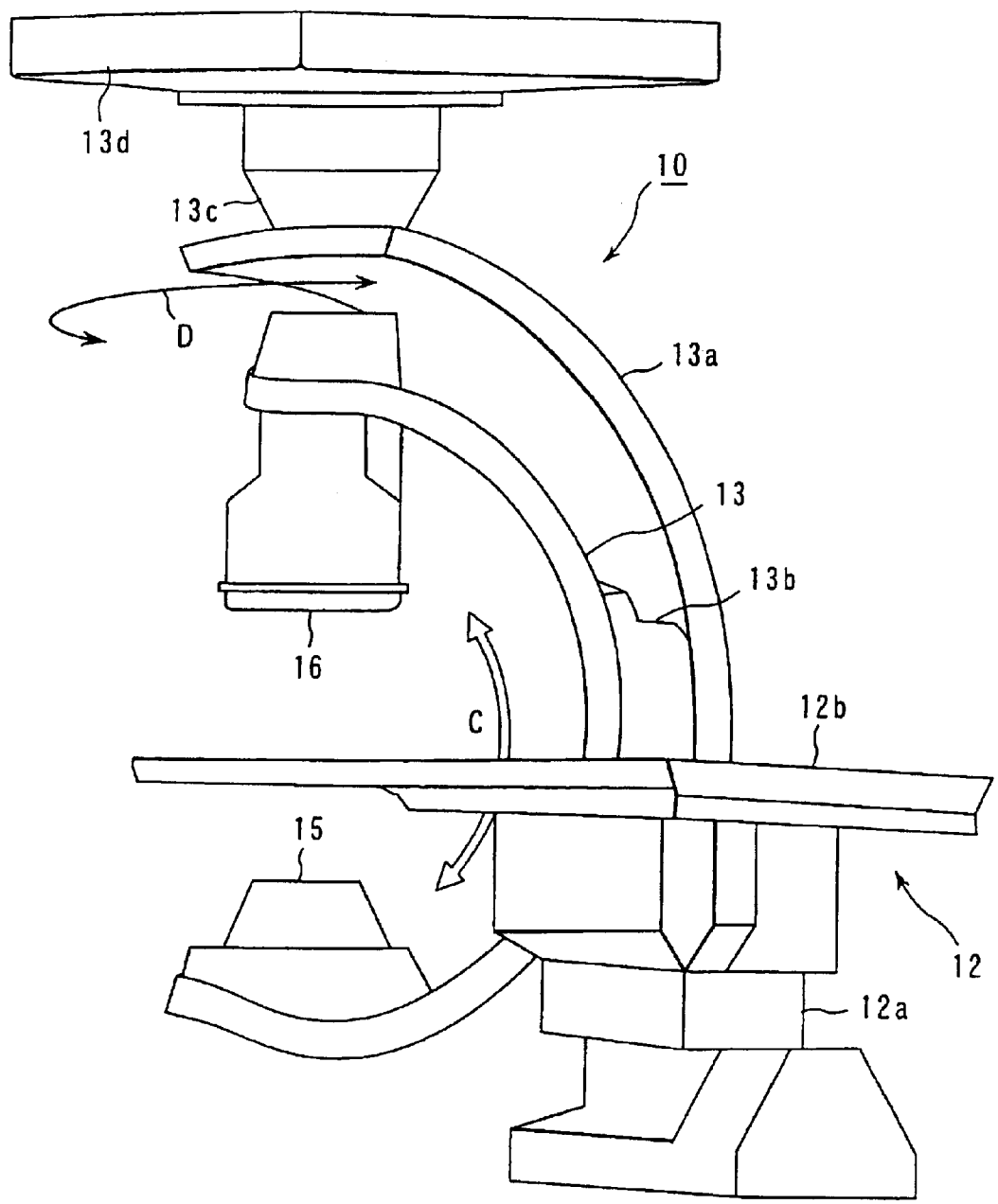
FIG. 1 is a schematic view showing the overall arrangement of as X-ray diagnosis apparatus 10 according to embodiments.

An embodiment of the present invention will be described below with reference to the views of the accompanying drawing. In the following description, components having the same function and arrangement will be denoted by like reference numerals and repeated descriptions thereof are given only when necessary.

Figure 2:
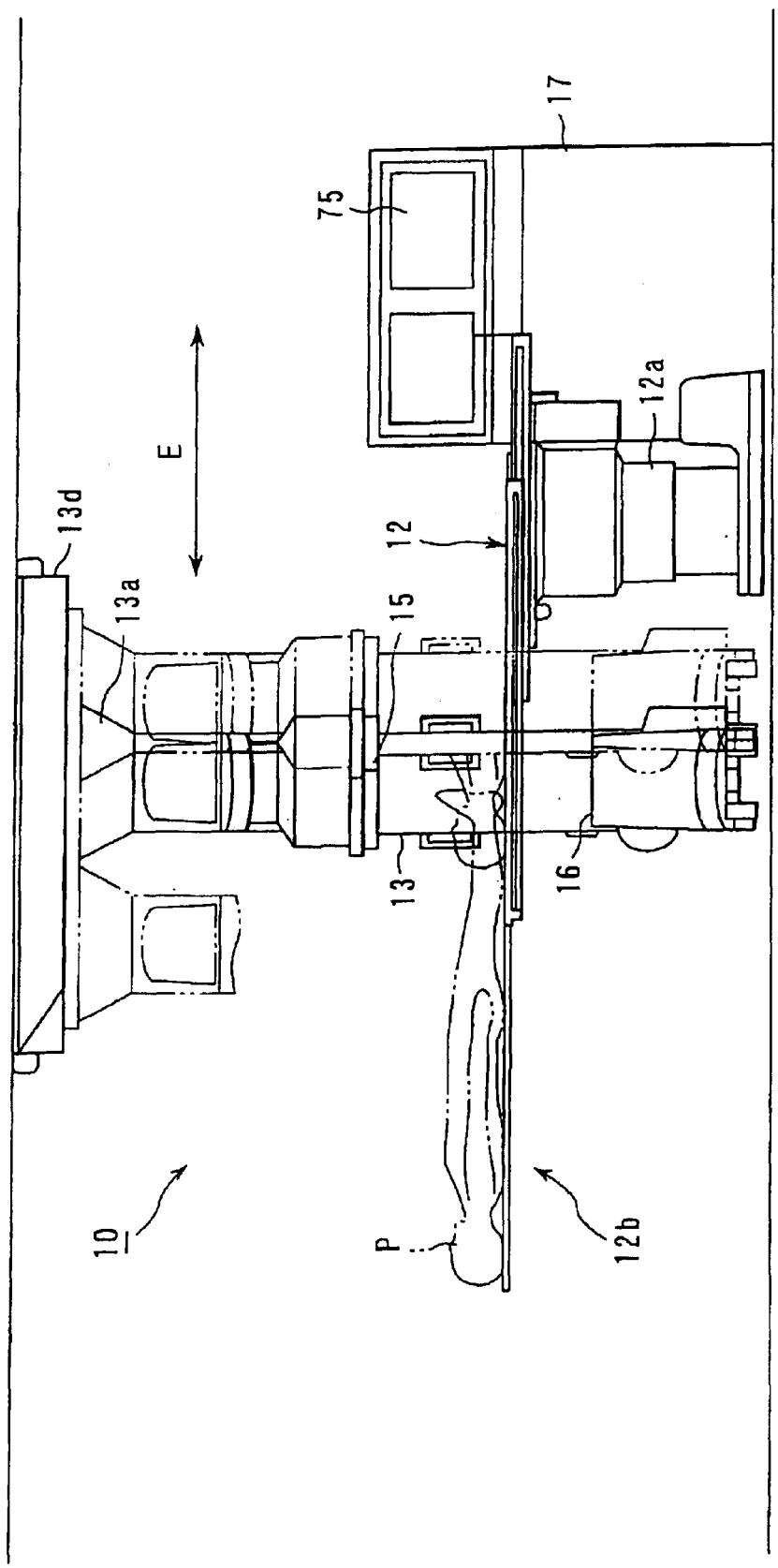
FIG. 2 is a side view the X-ray diagnosis apparatus 10 in FIG. 1.

FIG. 1 is a schematic view showing the overall arrangement of an X-ray image diagnosis apparatus that has an outward appearance similar to conventional diagnosis apparatus, which lack the movement capability illustrated as arrows C–E here and in FIG. 2. FIG. 2 is a side view of the apparatus. Assume that in this embodiment, the present invention is applied to a so-called "angiography apparatus".

Note that, the "angiography apparatus" has been described as an example of the "X-ray diagnosis apparatus" according to each embodiment described below. However, the present invention is not limited to such a form. For example, the present invention can be applied to a so-called "fluoroscopic imaging apparatus" and "multi-purpose X-ray image diagnosis apparatus".

As shown in FIG. 1 and FIG. 2, an angiography apparatus 10 (that is X-ray diagnosis apparatus 10) comprises a bed 12, a substantially C-shaped support unit (to be referred to as a "C-arm" hereinafter) 13, a fixed arm 3a, a connecting portion 3b, a support mechanism 13c, a base 3d, an X-ray generator 15, an X-ray detector 16 and an image processing apparatus 17.

The bed 12 is a bed to lay a patient to be examined and, as shown in FIG. 1 and FIG. 2, includes a foot 12a and a top 12b mounted on the foot 12a. The top 12b can move along the longitudinal direction (as indicated by an arrow E in FIG. 2) of the patient. Generally, the patient is laid on the bed 12 in such a manner that the longitudinal direction corresponds to the body axis of the patient in a diagnosis. Therefore, the patient lies down on the bed 12 can be moved in the longitudinal direction (along the body axis). The foot 12a is preferably installed in a place where it does not interfere with the operation/movement of the C-arm 13. From this point of view, as shown in FIG. 1 or 2, substantially rectangular parallelepiped foot 12a is installed along an end portion of the bed 12. The foot 12a of the X-ray diagnosis apparatus 10 is fixed. Accordingly, the patient on the bed 12 can be moved by only movement mechanism of the top 12b. However, the present invention is limited to this. For example, the foot 12a itself may be capable to moving up and down. The bed 12 can take various other forms.

The C-arm 13 is a substantially C-shaped support unit and includes the X-ray tube 15 on one end and the X-ray detector 16 on the other end. The C-arm 13, referring to FIG. 1, is connected to the fixed arm 13a that is mounted to externally cover the c-arm 13 through a connecting portion 13b. One end of the fixed arm 13a is rotatably mounted on a support mechanism 13c formed on the ceiling through a base 13d. The C-arm 13 and the fixed arm 13a can rotate on the support mechanism 13c, as indicated by arrow C in FIG. 1. In addition, the C-arm 13 can move in the longitudinal direction indicated by an arrow E in FIG. 2 by movement of the base 13d along a rail (not shown). Furthermore, the C-arm 13 can perform combination of movement in each direction C, D and E.

Note that, the X-ray diagnosis apparatus 10 has a C-arm driver 82 (see FIG. 3), which allows the C-arm 13 to move in each of directions indicated by the arrows c, D and E in FIG. 1.

Moreover, the movement mechanism of the C-arm 13 described above, is a merely an example. Therefore, the embodiments of the present invention is limited to this form. For example, according to the above description, the C-arm 13 is designed to move in the longitudinal direction as the base 13d travels along a rail installed on the ceiling, i.e., on the basis of a so-called overhead traveling scheme. In the present invention, however, the C-arm 13 may be moved in the longitudinal direction indicated by preparing another member that is installed on the floor surface to hold the C-arm 13 and moving the member along the floor surface.

The position information in each directions of C, D and E is detected by a position detector 80 (see FIG. 3) as described later and transmitted to a data acquisition section 71 as a part of diagnosis information or imaging information. Note that, the position information offers the relative position of the C-arm 13 to the bed 12 (or the patient) and is, for example, the distance from the predetermined point in each of the directions C, D and E, the position coordinate, the rotational angle or the like. The position information of each of the directions C, D and E have to be determined to define the three dimensional position of the C-arm 13.

The X-ray tube 15 is a vacuum bulb which generates X-ray and is arranged on one end of the C-arm 13. The X-ray tube 15 emits X-ray when electrons accelerated by a high voltage generator (not shown) are bombarded with a target in the X-ray tube 15.

The X-ray detector 16 is I.I. (Image Intensifier) which converts X-ray emitted form the X-ray tube 15 and passed through the patient body to an optical image. The X-ray detector 16 is installed on the other end of the C-arm 13 and placed opposite to the X-ray tube 15. In diagnosis, the c-arm is placed in such a way that the patient or the bed 12 is sandwiched between the X-ray tube 15 and the X-ray detector 16. Hereinafter, the state that the bed 12 is sandwiched between the X-ray tube 15 and the X-ray detector 16 is referred to as "normal state".

Note that, the X-ray detector 16 is I.I. in this embodiment. However, the present embodiment is limited to this form. obviously, for example, as the X-ray detector 16, a so-called "FPD (Flat Panel Detector)" may be used.

The image processing apparatus 17 performs a predetermined processing to X-ray imaging data and generates a mask image, a contrast image, a subtraction image or the like. These images are stored in a memory, disk (not shown) or the like in the image processing apparatus 17 (see FIG. 3).

Figure 3:
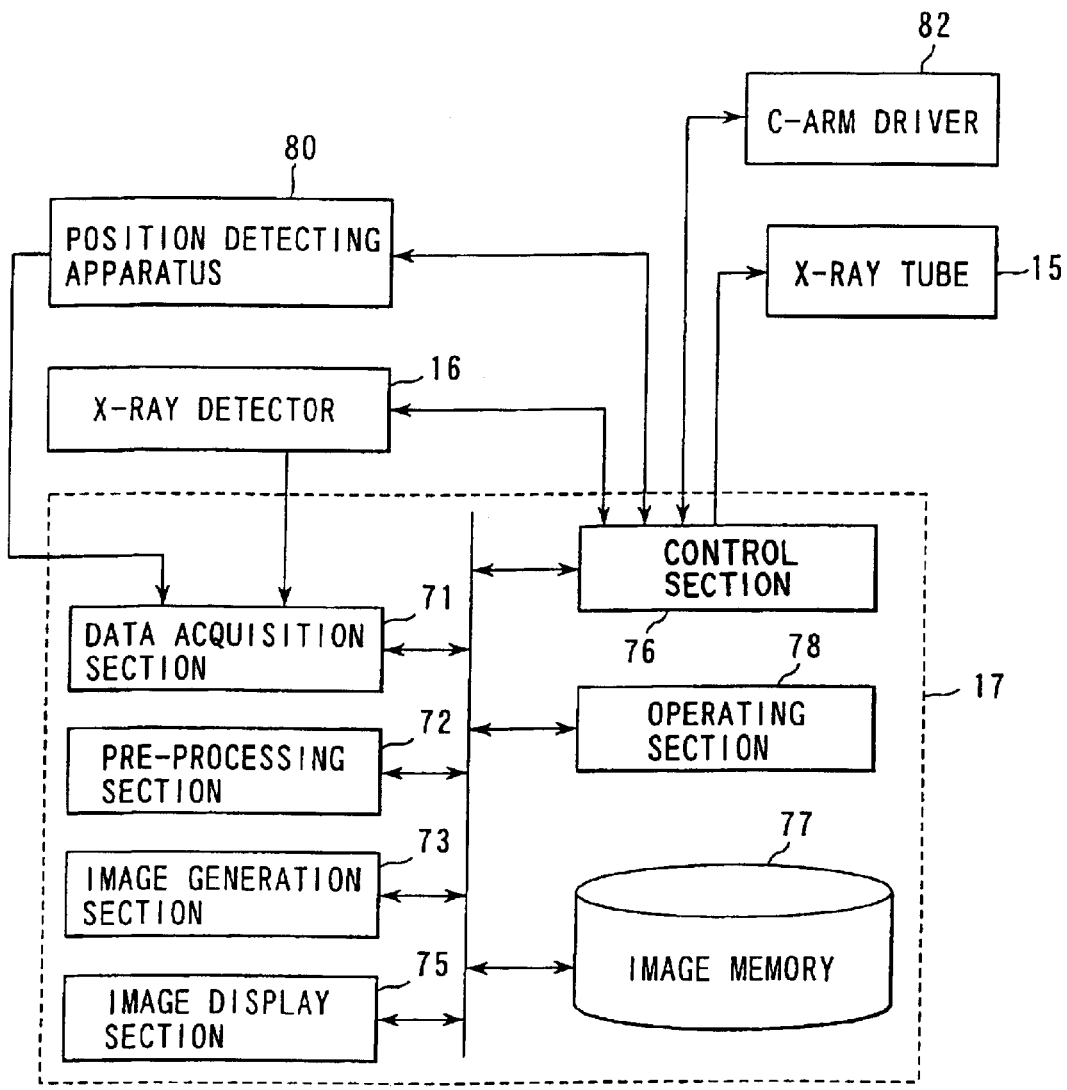
FIG. 3 is an example of a block diagram of X-ray diagnosis apparatus 10.

FIG. 3 is a block diagram of X-ray diagnosis apparatus 10.

The angiography apparatus 10 comprises a data acquisition section 71, a pre-processing section 72, an image generation section 73, an image display section 75, a control section 76, an image memory 77, an operating section 79, a position detecting apparatus 80 and a C-arm driver 82.

The data acquisition section 71 acquires X-ray data input from the X-ray detector 16 and converts the data into a digital signal. The data acquisition section 71 acquires the position information of the C-arm 13 which changes due to the effects of the C-arm driver 82. Each of the position information is added to the image of each flame and managed as attribute information.

The pre-processing section 72 performs calibration processing and the like for X-ray data which is digitally converted by the data acquisition section 71.

The image generation section 73 generates a mask image, a contrast image and a subtraction image on the basis of the image data output from the pre-processing section 72. Specifically, the image generation section 73 generates the subtraction image by subtracting the mask image from the contrast image.

The image display section is a display device, such as CRT or the like, for displaying a X-ray image generated by the image generation section.

The control section 76 controls operation of angiography apparatus 10. For example, when an instruction of the movement of the C-arm 13 is input through a jog-shuttle (after mentioned) in arbitrary timing, the control section 76 controls the C-arm driver 82 according to the instruction. In addition, the control section 76 controls generation of an image, storage, or the like on the basis of the contents of a command received from the operating section 78, or controls the operation of the bed 12, C-arm 13, or the like.

The image memory 77 stores a X-ray image generated by the image generation section 73.

Figure 4:
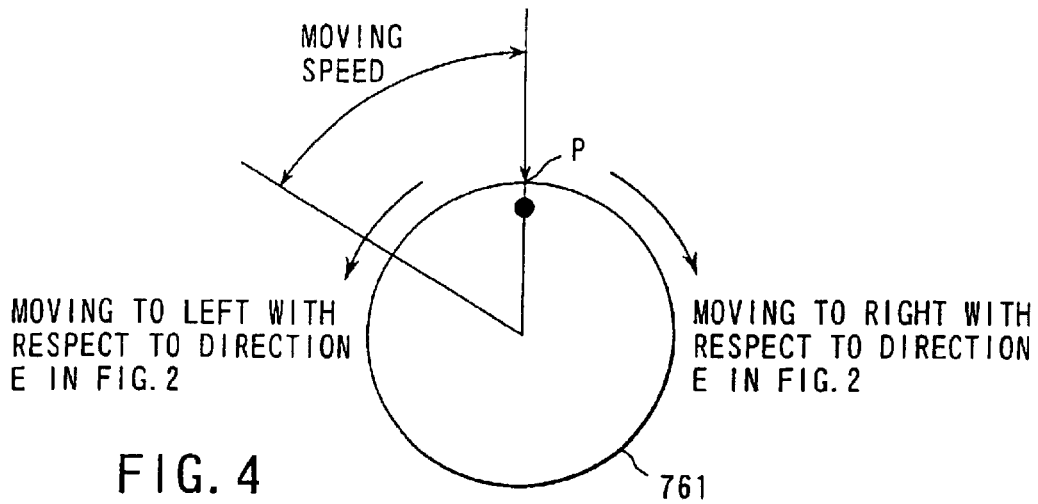
FIG. 4 shows a jog-shuttle arranged in X-ray diagnosis apparatus.

The operating section 78 has a keyboard, various switches, mouse, and the like. In addition, the operating section 78 has an interface used by an operator to input various instructions with respect to the movement of the C-arm 13 and the like. More specifically, a joystick, shown in FIG. 4, can be used as the interface. For example, the input of the instruction with respect to the movement of the C-arm 13 in the direction E in FIG. 4 can be performed as follows:

In FIG. 4, for example, the rotational direction of the jog-shuttle 781 from a reference position P corresponds to the lateral moving direction in FIG. 2. That is, when the jog-shuttle 781 is rotated clockwise (or counterclockwise), the C-arm 13 moves to the right (or left) in FIG. 2. In addition, as the rotational angle increases, the moving speed of the C-arm 13 increases. Note that if the operator releases his/her hold of the jog-shuttle 781 in FIG. 4 when it is rotated to a predetermined position, the jog-shuttle 781 is biased to automatically return to the reference position P.

Note that, the interface to input an instruction of movement of the C-arm is limited to the jog-shuttle 781. More specifically, a joystick, arrow buttons, or the like can be used as the input means. The operating section 78 may take various forms other than those described above.

The position detecting apparatus 80 detect a position information of the C-arm 13. For example, the position detecting apparatus 80 may be implemented by a so-called absolute encoder based on a magnetic scheme, brush scheme, photoelectric scheme, or the like. The present invention is not limited to any specific type of encoder, i.e., a rotary encoder or linear encoder.

The C-arm driver 82 is a power source at appropriate positions (not shown), which allows the C-arm 13 to move in each of the directions C, D, and E.

Next, the operation the angiography apparatus 10 in contrast medium chase imaging will be described referring to FIG. 5 and FIG. 6. In contrast medium chase imaging, the angiography apparatus 10 can perform X-ray imaging associated with angiography while allowing a doctor to conduct a surgical operation or examination, e.g., inserting a catheter. For the specific description, a case where constant medium chase is executed with respect to the lower extremities (both legs) of the patient will be described. In addition, in general, constant medium chase imaging has two styles. The first style is a mask first imaging style in which mask imaging is executed firstly and contrast imaging is executed secondly. The second style is a contrast first imaging style in which mask contrast is executed firstly and contrast imaging is executed secondly. For the specific description, a case of the mask first imaging style will be described. However, the same effect in a case of the contrast first imaging style can be obtained.

Figure 5:
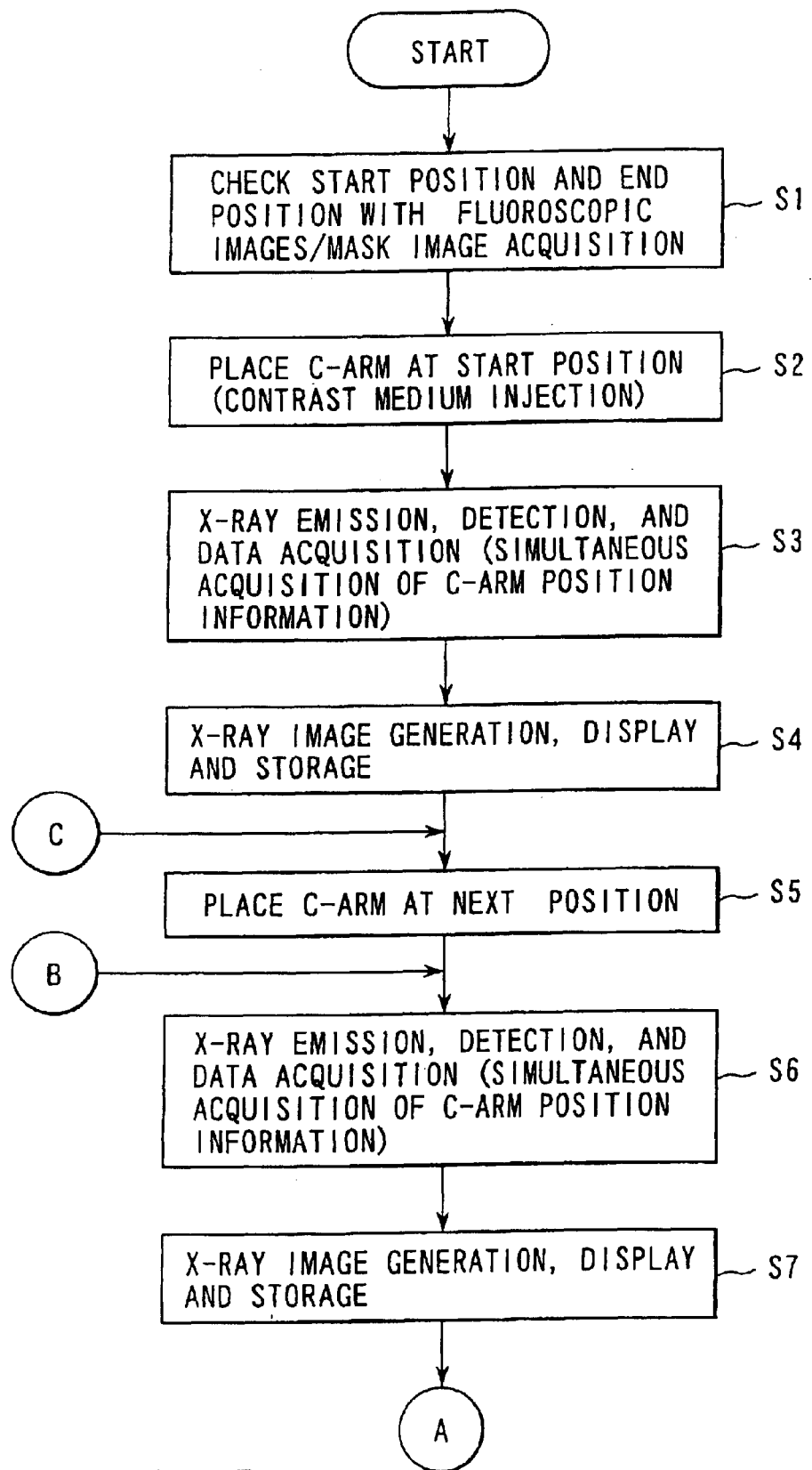
FIG. 5 is an example of a flow chart showing the process in constant medium chase imaging.
Figure 6:
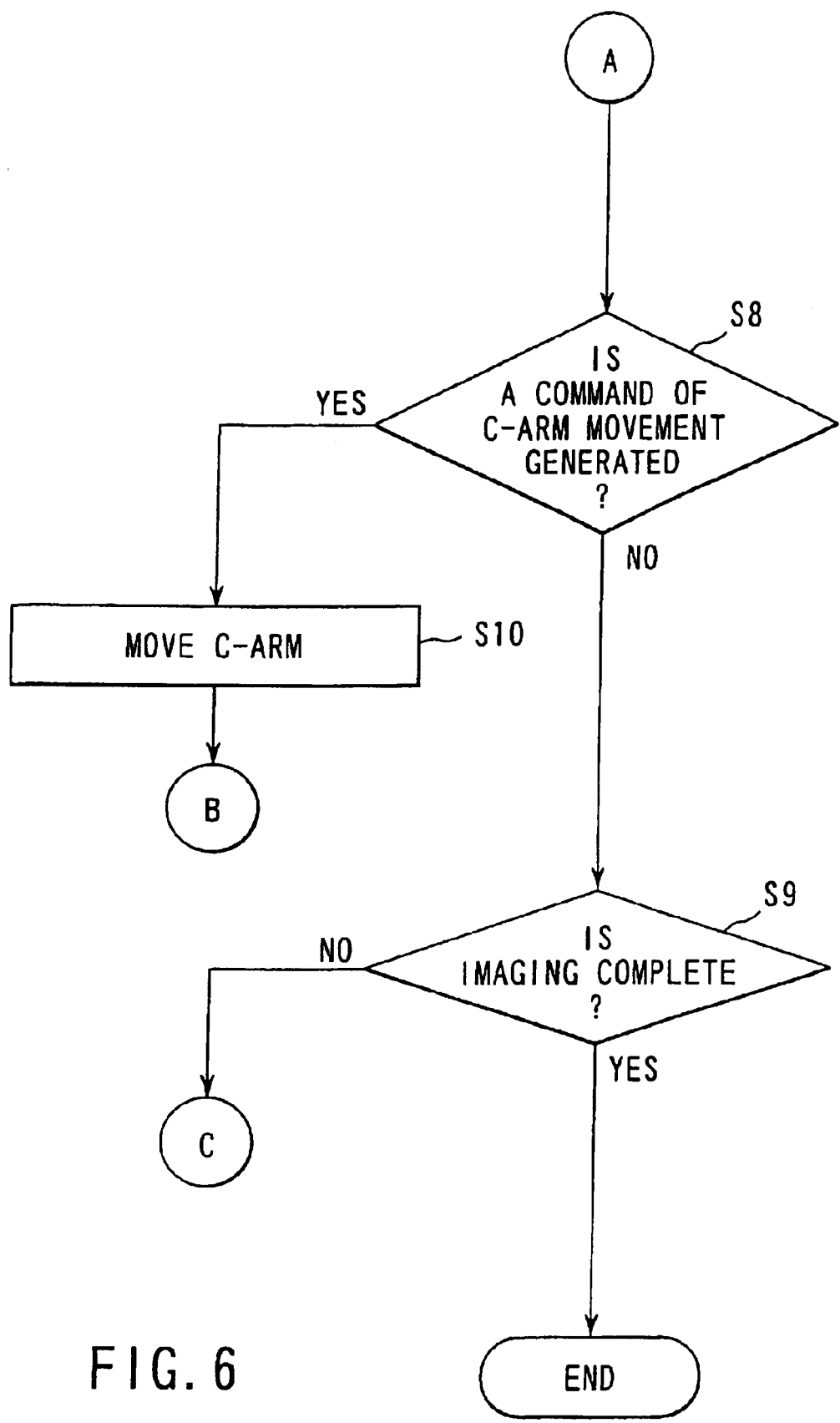
FIG. 6 is an example of a flow chart of a process in constant medium chase imaging.

FIG. 5 and FIG. 6 show flow charts of the process in constant medium chase imaging. In FIG. 5, first of all, the operator checks the start and end positions of constant medium chase imaging with a fluoroscope image after the patient laid down on the top 12b of the bed 12 (step S1). In this case, since lower extremity imaging is executed, the start position coincides with the abdomen of the patient, which generally corresponds to the injection position of a contrast medium, and the end position coincides with the end portions of the two legs, i.e., the "tiptoes" portions or the like.

The operator then positions the C-arm 13 at the start position of contrast medium chase imaging, which has been determined, i.e., the abdomen of the patient (step 2). In this case, a contrast medium is injected into the patient.

Then X-ray emitting of the X-ray tube 15 at a predetermined timing (or a predetermined position), the X-ray detecting and data acquisition are executed in accordance with the manner in which the contrast medium flows in the lower extremities of the patient (step S3). At the timing of the X-ray emitting, the position information of the C-arm 13 is output from the position detecting apparatus 80 and added to the image data corresponding to the X-ray emitting.

Then image generation, display and storage are executed on the basis of the acquired data (step S4). In the above image generation processing, the following two modes can be executed in this embodiment.

The first mode is the DA (Digital Angiography) mode of executing general X-ray imaging. In this mode, an X-ray image including a contrast medium (its flow) is simply acquired and displayed/stored.

The second mode is the DSA (Digital Subtraction Angiography) mode of displaying/storing an X-ray image showing a contrast medium and the manner in which it flows more clearly by acquiring (subtraction processing) a difference image between an X-ray image (mask image) including no contrast medium (image) and an X-ray image (contrast image or live image) including the contrast medium (image). In the present invention, the basic function and effect of imaging of each mode remain the same. That is, imaging can be executed in either the DA mode or the DSA mode. In the case of the above DSA mode, before a contrast medium is injected, a general X-ray image (i.e., the above mask image) associated with the lower extremities of the patient must be prepared.

In this subtraction procedure, in order to extract the contrast object appropriately, subtraction image has to be generated from mask image and contrast image to each of which the identical position information is added. Therefore, in mask first imaging style the contrast image has to be acquired in the position identical with the position of acquiring the mask image and in contrast first imaging style vice versa. This identification between the position of acquiring the mask image and the position of acquiring the contrast image can be performed by emitting x-ray at the position of acquiring the mask image on the basis of the position information added to the mask image. In other words, the control section 76 controls a timing of X-ray emitting according to the position information added to the mask image and a position information of the C-arm 13 detected the position detecting apparatus 80 in step 3. In this case, the operator need not give any special attention to this operation, and appropriate contrast image acquisition and subtraction processing are performed on the apparatus side.

Then the C-arm 13 is positioned at a next position (step S5). In the DSA mode, described above, the next position is determined on the basis of the position information added to the mask image.

After the C-arm 13 is positioned at the next position, X-ray emitting, the X-ray detecting and data acquisition are executed (step S6), and furthermore, image generation, display, and storage are executed (step S7).

Referring to FIG. 6, the control section 76 determines whether a command to move the C-arm 13 through the jog-shuttle is executed or not (step S8).

When the control section 76 determines that the command to move the C-arm 13 is executed in step S8, the C-arm is moved in accordance with the command (step S10). After the C-arm is positioned at a predetermined position, X-ray emitting, the X-ray detecting and data acquisition are executed (step S6), and furthermore, image generation, display, and storage are executed (step S7).

In the case of determining that the command to move the C-arm 13 is not executed in step S8, the control section 76 determines whether the imaging is completed or not (step S9). In the case where the imaging is not completed and the command to move the C-arm 13 is not executed, the imaging is executed at the same position without movement of the C-arm at a predetermined rate. On the other hand, in the case where the imaging is not completed and the command to move the C-arm 13 is executed, the process in constant medium chase imaging is shifted to step S5 and, for example, the imaging is executed at a next position.

Figure 7A:
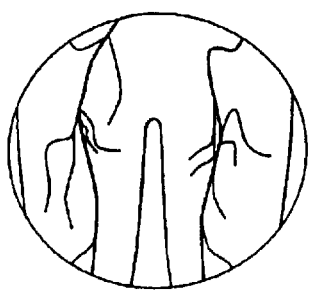
FIGS. 7A to 7E are examples of contrast images acquired by X-ray diagnosis apparatus.
Figure 7B:
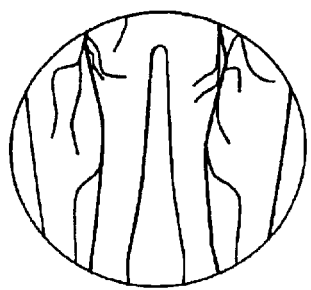
Figure 7C:
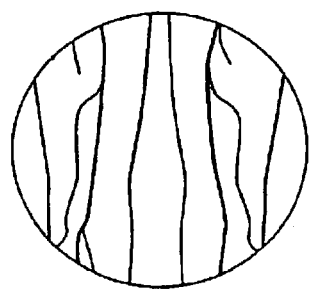
Figure 7D:
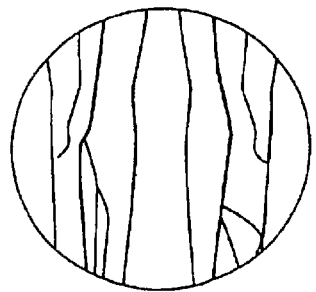
Figure 7E:
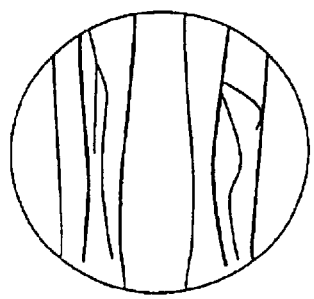

Subsequently, the operator may repeatedly execute the above operation until contrast imaging is completed. For example, FIGS. 7A to 7E show the images acquired in this manner, which include five images that allow the operator to check the manner in which a contrast medium flows from a position near the abdomen of the patient (FIG. 7A) to positions near the end portions of the two legs (FIG. 7E). Obviously, they are merely examples. In practice, the number of images to be acquired is not limited.

Figure 8:
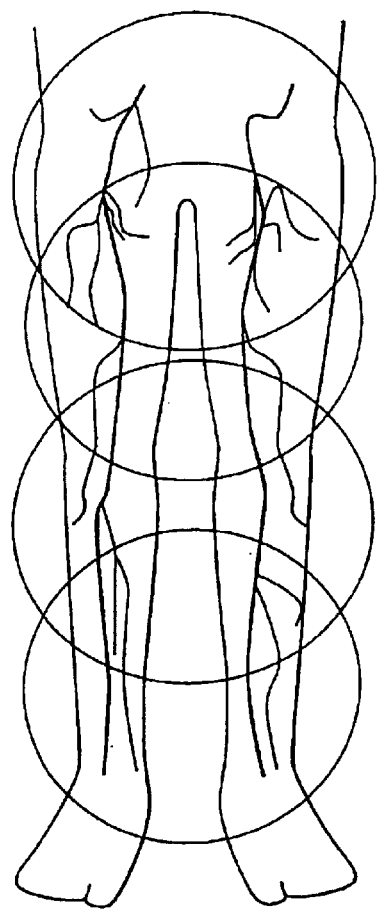
FIG. 8 is a plurality of angiography pasted together by X-ray diagnosis apparatus.

Note that, described above, each of images acquired with the angiography apparatus 10 and stored in the image memory 77 corresponds to the position information. Therefore, as shown in FIG. 8, the images acquired at a plurality of regions of the patient P can be pasted together on the basis of the position informations and displayed. This allows the operator to check the overall blood vessels.

Figure 9A:
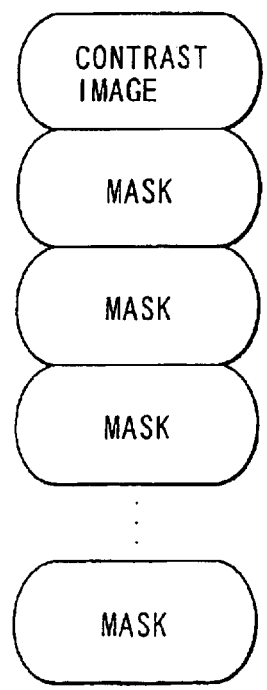
FIGS. 9A to 9C are schematic views showing an example of how the X-ray images acquired by constant medium chase imaging in the DSA mode are pasted together and displayed and an example of how the flow of a constant medium is reproduced/displayed.
Figure 9B:
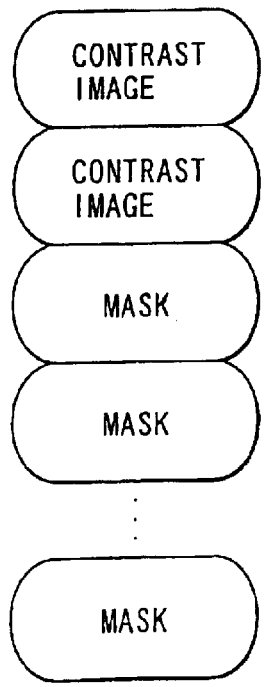
Figure 9C:
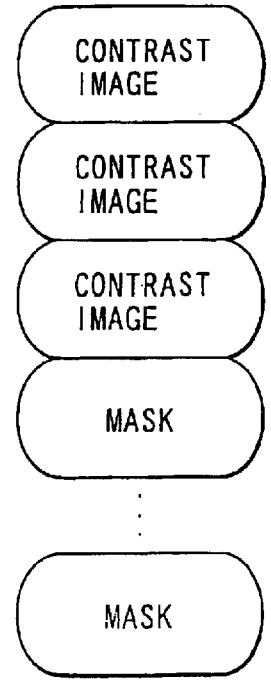
Figure 10E:
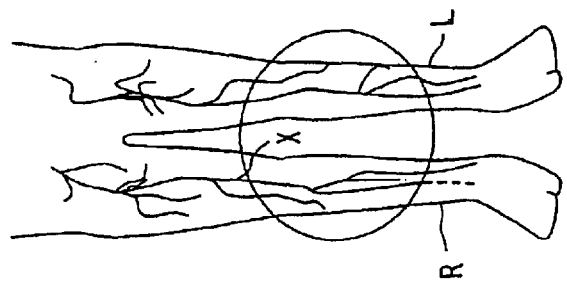
FIGS. 10A to 10E are views for explaining how imaging is executed when a portion of a blood vessel in one leg of a patient to be examined is constricted.
Figure 10D:
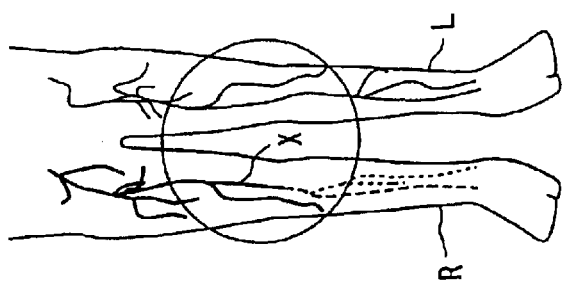
Figure 10C:
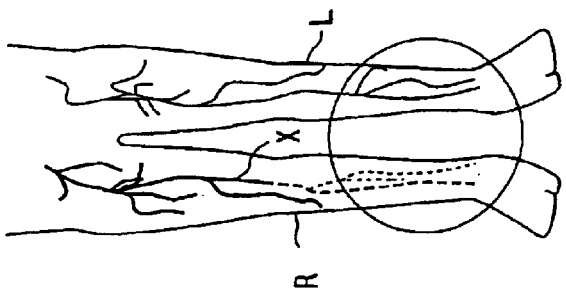
Figure 10B:
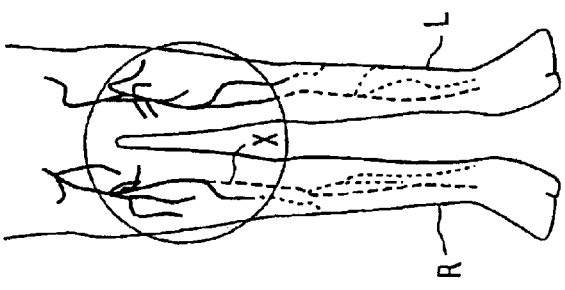
Figure 10A:
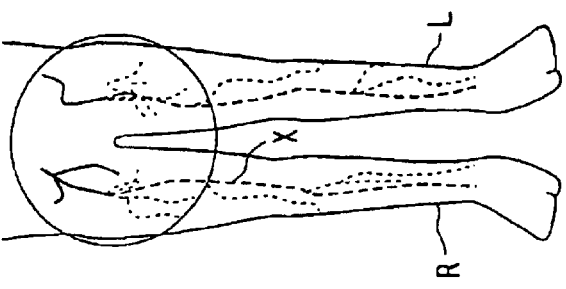

If contrast medium chase imaging is executed in the above DSA mode, in particular, the following processing can also be executed with respect to the image shown in FIGS. 9A to 9C. In the DSA mode, as described above, a mask image including no contrast medium image and a contrast image including a contrast medium image exist at the same position coordinates. If, therefore, display operation is performed such that mask images are sequentially (one by one) converted into contrast images as shown in FIGS. 10A to 10C, the flow of a contrast medium can be reproduced on the image display section D. Such a display form will be termed as "bolus cine display". In this case, a more realistic image of the flow of a contrast medium can be reproduced by matching the above sequentially changing speed (image switching speed) to the speed at which actual X-ray images are acquired.

As has been described above, one of characteristic points in this embodiment is that the C-arm 13 can be moved in the "desired direction" at "arbitrary timing, i.e., "a desired direction with respect to the body axis direction of the patient" in lower extremity imaging. This point will be described in more detail below.

Assume that a portion of a blood vessel in one leg of the patient has become constricted, and a contrast medium does not flow normally in the leg. In this case, the angiography apparatus 1 in this embodiment can execute X-ray imaging like that shown in FIGS. 10A to 10E. Referring to FIG. 10A to 10E, the blood vessels which the contrast medium has not reached are indicated by the dashed lines, and those which the contrast medium has reached are indicated by the solid lines. Furthermore, the circle in FIGS. 10A to 10E represents the imaging field of view FV at each imaging position. The imaging field of view FV can be adjusted to a desired size.

First of all, referring to FIG. 10A, X-ray images of two legs R and L of the patient are acquired at positions near the imaging start position. As shown in FIG. 10B, an image associated with one leg R in which it is recognized that the contrast medium has reached a constricted region X and flows inappropriately is acquired, together with an image of the other leg L in which no special anomaly is recognized, i.e., the leg L in which the contrast medium flows without stagnation.

Next, as shown in FIG. 10C, to execute X-ray imaging of the leg L, the operator moves the C-arm 13 in the same direction as that described above, i.e., toward the tiptoes, thus acquiring a contrast medium chase sensed image of the leg L. When the operator ascertains the flow of the contrast medium in the leg L in this manner, he/she moves the C-arm 13 in the direction of the abdomen opposite to the direction described above, thereby executing X-ray imaging of the constricted region X (the leg R in which the contrast medium flows inappropriately). In this case, if imaging has been executed in the above "DSA model", the mask image position is accurately matched to the contrast image acquisition position, thus executing subtraction processing in real time. After such imaging, as shown in FIG. 10E again, the operator moves the C-arm 13 toward the tiptoes again to perform X-ray imaging of the leg L in which the contrast medium flows normally. This makes it possible to execute X-ray imaging.

In addition, if there is a occlusion of a portion of a blood vessel in one leg of the patient, X-ray imaging like that shown in FIGS. 11A to 11D can be done.

Figure 11A:
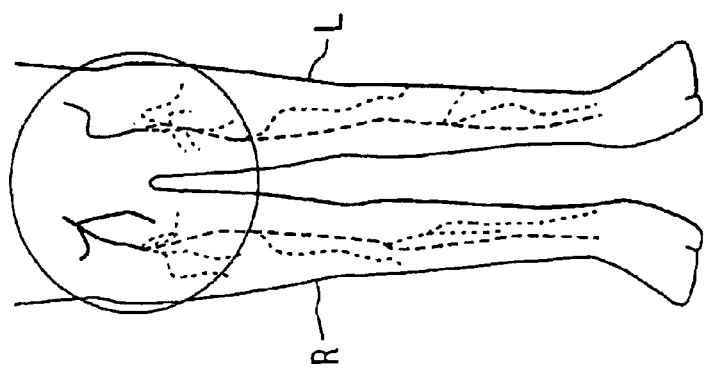
FIGS. 11A to 11D are views for showing how imaging is executed when a portion of a blood vessel in one leg of a patient to be explained is occluded.
Figure 11B:
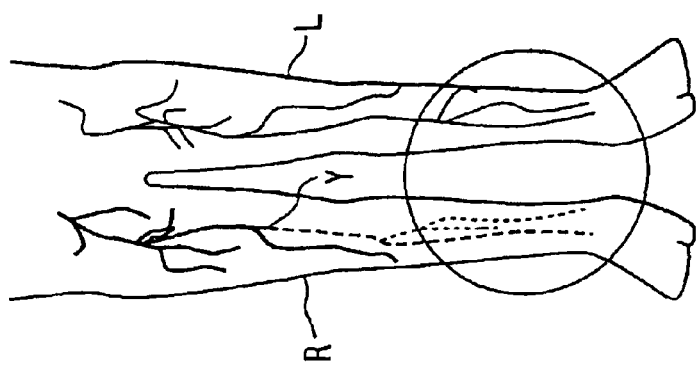
Figure 11C:
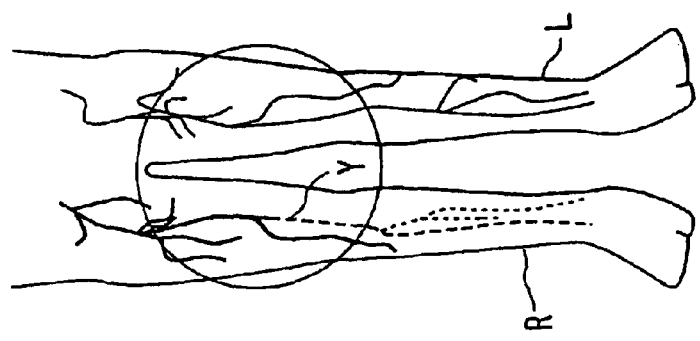
Figure 11D:
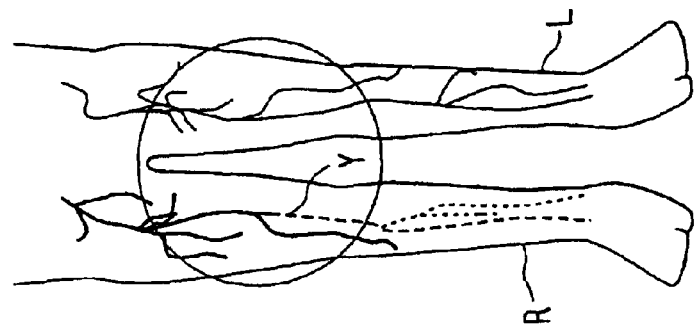

The concept shown in FIGS. 10A to 10E applies to this case. According to the angiography apparatus 10 in this embodiment, X-ray imaging of a region Y where an occlusion has occurred can be continuously done, as shown in FIGS. 11C and 11D. More specifically, after X-ray imaging of the leg L in which the contrast medium flows without stagnation is executed from the abdomen to the tiptoe portions (from FIG. 11A to FIG. 11B), "the C-arm 13 is returned" from the tiptoe portions to the region Y of the leg Pa in which an occlusion is suspected (from FIG. 11B to FIG. 11C) and is held at the region, thereby executing continuous X-ray imaging (FIGS. 11C and 11D). This means that a region in which an occlusion is suspected can be accurately examined.

As described above, according to the angiography apparatus 10 in this embodiment, the operator can execute contrast medium chase imaging while changing the position of the C-arm 13 arbitrarily. This eliminates the necessity to execute imaging again as in the prior art and can limit the number of times the patient is exposed to X-rays and injected with a contrast medium to only one.

According to the angiography apparatus 10 in this embodiment, in particular, since position coordinates as the attribute information of images are sequentially acquired in accordance with the movement of the C-arm 13 or the execution of imaging, the operator can execute imaging while moving the C-arm 13 in the "desired direction" even in the DSA mode as in the above manner. This makes it possible to reduce the burden imposed on the patient.

Second Embodiment

The second embodiment of the present invention will be described below. The second embodiment is associated with simulation mode of contrast medium chase imaging.

In general, since contrast media flow differently at different flow rates in different patients, operators often fail imaging in practice. Therefore, proper contrast medium chase imaging for each patient is acquired. Under this circumstances, contrast medium chase imaging is a relatively sophisticated imaging technique and demands a certain degree of skill.

The present angiography apparatus 10 can perform the simulation mode for simulating contrast medium chase imaging. With this simulation mode, before the actual contrast medium chase imaging is started, the operator can be given the confidence to do imaging and grasp an actual feeling of imaging. In addition, this eliminates the necessity to expose the patient to X-rays again and inject him or her with a contrast medium again as required in re-imaging operation, and hence save an unnecessary burden on the patient.

Figure 12:
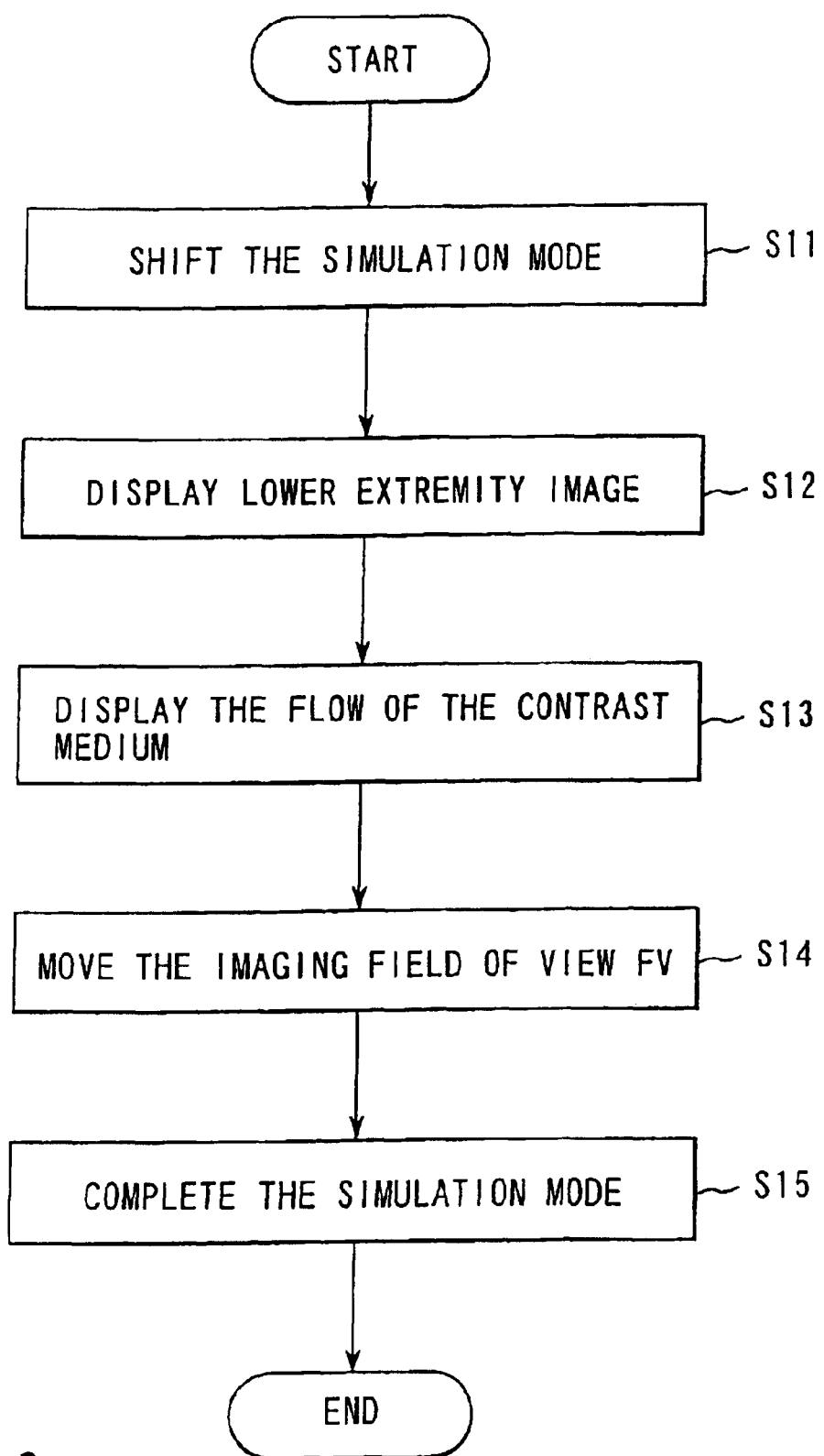
FIG. 12 is a view for explaining an action of the X-ray diagnosis apparatus 10 in the simulation mode.

FIG. 12 is a view for explaining an action of the x-ray diagnosis apparatus 10 in the simulation mode. The simulation mode of the angiography apparatus 10 will be described below with reference to FIG. 12.

First of all, the operation mode of the angiography apparatus 10 is shifted to simulation mode in response to a predetermined instruction (step S11). The image display section 75 reproduces a lower extremity image (x-ray image associated with a predetermined region) by pasting images fluoroscopically sensed in step S1 in FIG. 5, images acquired at past, simulated image for simulation (This is not limited to a X-ray image.) or the like together. The lower extremity image LLF of the patient is displayed on the image display section 75, as shown in FIG. 11 (step S12). A simulated imaging field of view FV is superimposed on this reproduced lower extremity image LLF.

Figure 13:
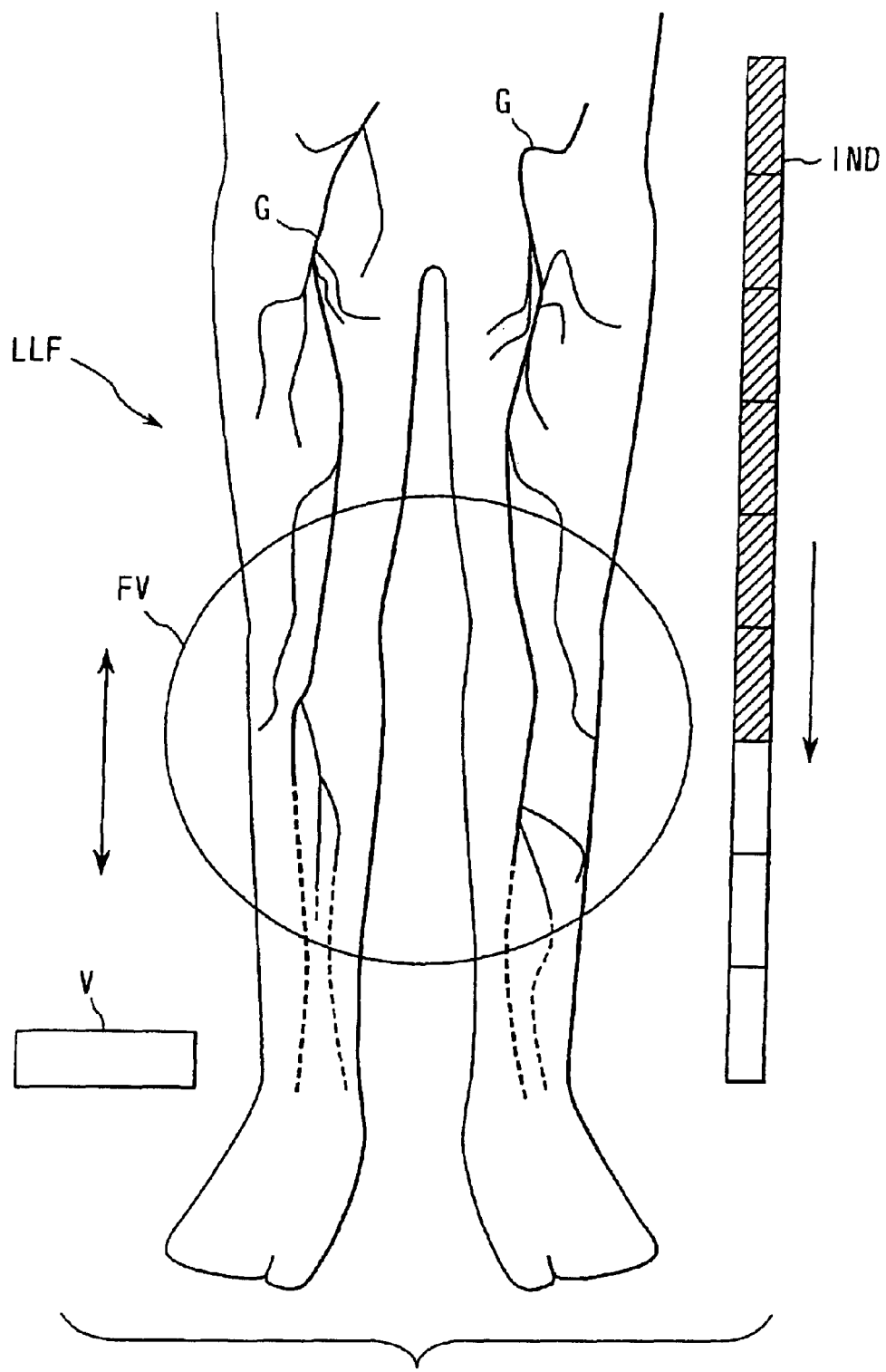
FIG. 13 is a schematic view showing an example of a displayed image in the simulation mode.
Figure 14:
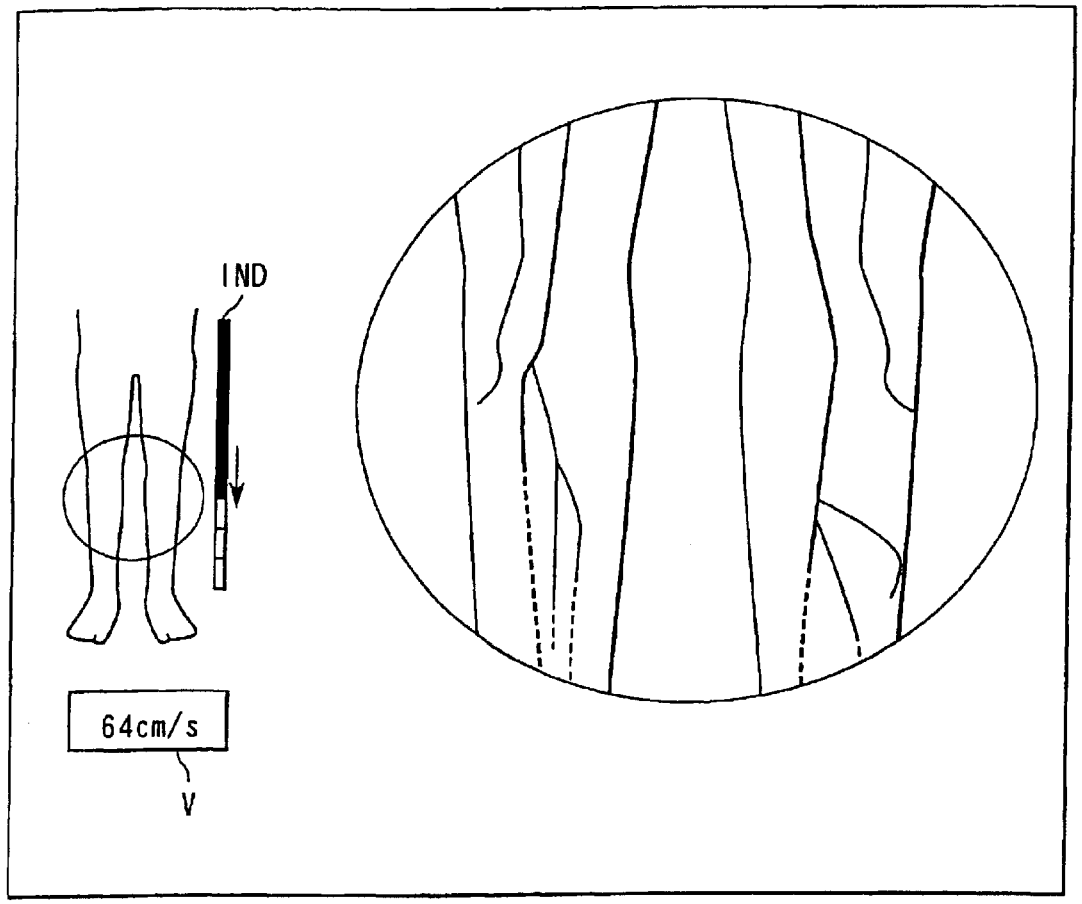
FIG. 14 is a schematic view showing an example of a displayed image in the simulation mode.

FIG. 13 and FIG. 14 are schematic views showing an example of a displayed image in the simulation mode. Note that the solid lines indicate the presence of a contrast medium and the dashed lines indicate the absence of a contrast medium in FIGS. 13 and 14.

On the lower extremity image LLF, graphics display of a simulated flow of the contrast medium is performed in accordance with the region in which blood vessels run (step S13). For example, this graphics display of a simulated flow can be performed by displaying the images in which a contrast medium flows in blood vessels gradually. With graphics display the simulated flow, the operator can observe an image in which the contrast medium looks as if it actually flowed.

In step S13, instead of/in addition to graphics display of a simulated flow, simple indicator display IND (constituted by a plurality of block displays, and lower blocks are sequentially inverted/displayed with time) may be performed, as shown in FIG. 13 and FIG. 14, thereby simulating the flow of the contrast medium. With this operation, the same effect as that described above can be obtained.

In addition, the above "contrast medium flow" in step S13 may be slowly or quickly adjusted by the operator as needed. This adjustment can be performed by adjusting the time interval of display a image including a simulated flow of the contrast medium on the image display device. Furthermore, it is convenient if the flow of a contrast medium obtained in the above manner, i.e., the exact numerical value of the flow rate, is displayed on the image display section D (see reference symbol V in FIGS. 13 and 14).

When the operator operates the jog-shuttle 781 in accordance with the simulated contrast medium flow, move the imaging field of view FV moves corresponding to the jog-shuttle operation to simulate actual contrast medium chase imaging (step S14). With this configuration, the operator can grasp the correspondence between the operation of the jog-shuttle 781 and the movement of the imaging field of view FV.

At this time, for example, the operator checks the intervals of X-ray image acquisition (=which regions of the patient P the operator should perform X-ray imaging) and the imaging field of view FV. In this case, the C-arm 3 may be simultaneously moved. This allows the operator to grasp an actual feeling of imaging. Obviously, however, no X-rays should be emitted from the X-ray tube 15 in this case.

If the simulation mode is completed in this manner, actual contrast medium chase imaging is performed according to the above procedure in the first embodiment. This allows the operator to start actual imaging while having a fresh feeling of completing actual contrast medium chase imaging, thus allowing the operator to execute imaging with less failures. This also makes it possible to save an unnecessary burden on the patient.

Such "flow of a contrast medium" may be expressed with a so-called "standard" flow rate obtained by averaging flow rates in a plurality of patients. In this case, the "standard flow rate" of a contrast medium may be obtained in the following manner.

First of all, the contrast medium flow rates in the respective patients are acquired on the basis of actual contrast medium chase imaging described above. If "imaging times" when the above image data were acquired are stored additionally like the position coordinates of image data described above, since the timer interval between the nth image acquisition and (n+1)th imaging acquisition can be known, the contrast medium flow rates of the respective patients can be easily known. The above "standard flow rate" can be obtained by simple arithmetic averaging of the check results on the respective patients which are acquired in the above manner. Note that if a "contrast medium flow rate database" is formed on the basis of the check results on the respective patients, this "standard" contrast medium flow rate can be easily obtained.

According to the X-ray image diagnosis apparatus described above, contrast medium chase imaging can be successfully completed with only one try basically without imposing an excessive burden of exposure to X-rays and injection of a contrast medium on a patient.

Note that, in the embodiment described above, the application of the present invention for bolus chase DSA method is explained. However, the present invention is not limited to this application. For example, the present invention can be applied to a so-called "rotational DSA method", and the same effects can be obtained. In this case, the position information of the C-arm 13 includes information with respect to rotational angle.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnosis apparatus comprising:
   a bed on which a patient lies down;
   a support unit including an X-ray generator configured to emit X-ray to the patient and an X-ray detector configured to detect the X-ray emitted form said X-ray generator;
   a movement mechanism configured to change a relative position of said support unit with respect to said the patient;
   a position detector configured to detect the relative position changed by the movement mechanism;
   a memory configured to acquire an information with respect to the relative position from said position detector at timing of the X-ray emitting by the X-ray generator and to store the information acquired as to a first image formed by emitting X-ray to the patient from the X-ray generator while the movement mechanism changes the relative position in a first direction;
   a controller configured to control timing of the X-ray emitting by the X-ray generator on the basis of the information stored in said memory when a second image is acquired by emitting X-ray to the patient injected with contrast medium while the movement mechanism changes the relative position in a second direction, in such a manner that the second image corresponds to the first image; and
   an image generator configured to generate a third image by subtracting the first image from the second image.

2. The X-ray diagnosis apparatus according to claim 1, further comprising:
   a controller configured to control said movement mechanism on the basis of the information of the relative position stored in said memory.

3. The X-ray diagnosis apparatus according to claim 2, further comprising:
   an interface configured to input at least a movement direction or velocity of said support unit; and
   wherein said controller controls said movement mechanism in response to the input movement direction or velocity of said support unit.

4. The X-ray diagnosis apparatus according to claim 2, further comprising:
   a display device configured to display a moving image which includes a plurality of the first images pasted to each other on the basis of the information.

5. The X-ray diagnosis apparatus according to claim 1, further comprising:
   a display device configured to display a moving image in which a contrast medium looks as if it actually flowed on the basis of the information; and
   an input device configured to move a field of view on the moving image in accordance with the flow of the contrast medium.

6. The X-ray diagnosis apparatus according to claim 5, wherein the moving image include at least one of the first image, the second image, the second image and a simulation image.

7. An X-ray diagnosis apparatus comprising:
- a memory configured to store a plurality of images each of which is added an information with respect to a relative position of a support unit with respect to a patient and includes a simulated flow of a contrast medium;
- an image generator configured to generate a moving image in which the contrast medium looks as if it actually flowed, by pasting the plurality of images together on the basis of the information;
- a display device configured to display the moving image; and
- an input device configured to move a field of view on the moving image in accordance with the flow of the contrast medium.

8. The X-ray diagnosis apparatus according to claim 7, wherein the moving image include at least one of a first image, a second image, the second image and a simulation image.

9. A control method of X-ray diagnosis apparatus comprising:
- acquiring a first image by emitting X-ray to a patient while changing a relative position of a support unit with respect to the patient in a first direction, the support unit including an X-ray generator and an X-ray detector configured to detect X-ray emitted from said X-ray generator;
- acquiring an information with respect to the relative position of said support unit with respect to said the patient at the timing of the X-ray emitting by the X-ray generator;
- storing the information acquired as to the first image;
- controlling movement of said support unit on the basis of the stored information;
- controlling timing of the X-ray emitting by the X-ray generator on the basis of the stored information when a second image is acquired by emitting X-ray to the patient injected with contrast medium while changing the relative position in a second direction, in such a manner that the second image corresponds to the first image; and
- generating a third image by subtracting the first image from the second image.

10. The control method of X-ray diagnosis apparatus according to claim 9, further comprising:
- in the case where movement direction or velocity of said support unit is input, controlling the said support unit in response to the input movement direction or velocity of said support unit.

11. An X-ray diagnosis apparatus comprising
- a bed on which a patient lies down;
- a support unit including an X-ray generator configured to emit X-ray to the patient and an X-ray detector configured to detect the X-ray emitted from said X-ray generator;
- a movement mechanism configured to change a relative position of said support unit with respect to said the patient;
- a position detector configured to detect the relative position changed by the movement mechanism;
- a memory configured to acquire information with respect to the relative position from said position detector at a timing corresponding to the timing of the X-ray emitting by the X-ray generator and to store the information acquired as to a first X-ray image when the first X-ray image is acquired by emitting X-ray to the patient while changing the relative position in a first direction; and
- a display device configured to display an X-ray image with apparent movement which includes a plurality of the first X-ray images pasted to each other on the basis of the information.

12. The X-ray diagnosis apparatus according to claim 11, wherein:
- said display device displays the apparently moving X-ray image as one in which a contrast medium looks as if it actually flowed on the basis of the information; and further comprising:
- an input device configured to move a field of view on the moving image in accordance with the flow of the contrast medium.

13. The X-ray diagnosis apparatus according to claim 12, wherein the moving image includes at least one of the first X-ray image, a second X-ray image, the second X-ray image and a simulation image.

* * * * *